United States Patent [19]

Augé et al.

[11] Patent Number: 4,549,358
[45] Date of Patent: Oct. 29, 1985

[54] APPARATUS FOR AUTOMATIC MEASUREMENT AND CLASSIFICATION OF CARCASES

[75] Inventors: Jean Augé, 1, rue Francois Sarre, 87350 Panazol, France; Jacques Lavaur, Gagnac-sur-Cere; Michel Assens, Montpellier, both of France

[73] Assignee: Jean Augé, Panazol, France

[21] Appl. No.: 614,242

[22] Filed: May 25, 1984

[30] Foreign Application Priority Data

May 27, 1983 [FR] France ................................ 83 08799

[51] Int. Cl.⁴ .............................................. G01B 7/28
[52] U.S. Cl. ....................................... 33/560; 33/511; 33/557
[58] Field of Search ............. 33/174 R, 174 P, 174 L, 33/174 PA

[56] References Cited

U.S. PATENT DOCUMENTS 3,593,427  7/1971  Abadotin ........................ 33/174 PA

FOREIGN PATENT DOCUMENTS 778552  7/1957  United Kingdom ........... 33/174 PA

Primary Examiner—Harry N. Haroian
Attorney, Agent, or Firm—Cushman, Darby & Cushman

[57] ABSTRACT

A fixed vertical stand (118) carries a frame (119) which can be displaced in a horizontal direction and in its slope with respect to the vertical, this frame (119) containing a plate (127) which slides in the vertical direction and is provided with a stop (135) having an upper reference face (136) intended for encountering the bone of the ischiopubic protuberance of a half-carcase, this plate (127) carrying diverse feelers which are emitters of position and displacement signals for the measurement of the various classification characteristics which are supplied to a calculator.

10 Claims, 4 Drawing Figures

APPARATUS FOR AUTOMATIC MEASUREMENT AND CLASSIFICATION OF CARCASES

FIELD OF THE INVENTION

The invention relates to an apparatus intended for automatically carrying out the measurement of the classification characteristics and for determination of the classification of the carcases of animals slaughtered for meat.

What is currently called the carcase is the body of a slaughtered animal which has been skinned and emptied of its internal organs, with its head and the end portions of its limbs removed. The apparatus of the invention is intended to be employed with half-carcases, that is to say, carcases split in two along a plane passing through the centre of the spinal column.

DESCRIPTION OF THE PRIOR ART

From the French patent application No. 2 335 845 an apparatus is known for measurement of the distances between the anatomical reference points on the carcase of an animal slaughtered for meat. Such an apparatus enables the dimensional characteristics to be taken off in the plane of section of a half-carcase but does not enable other important characteristics to be taken off, such as the rounding or the thickness of the rump steak, the thickness of the bulge of the topside, or the muscular thickness of the rib in carcases of beef, or else the outer development of the legs of veal or mutton, the muscular development of the loin (or kidneys) of veal or that of the loin (or back) of mutton. No more does it enable the volumetric characteristics to be taken off whole carcases of mutton or veal.

A device is also known from the West German patent application No. 2 602 524 for the measurement of half-carcases of pork in which feelers measure the contour of the hams and the thickness of the lard, the values of measurements being introduced into a programmed calculator to determine a quality class. Such an apparatus is adapted to only one type of animal and the placing of the half-carcase in position is the cause of waste of time.

Again, from the French patent application No. 2 488 530 an apparatus is known which serves for carrying out the measurement of the classification characteristics of the carcases of animals slaughtered for meat.

This apparatus comprises a vertical frame upon which feelers can be displaced vertically and horizontally, as well as means of relative positioning of this frame and the carcase being measured. In addition, a hinged flap opening out to 90° at one side of the vertical frame carries two arms movable vertically, along which other feelers can be displaced which are employed for the measurement of the muscular development of the rump steak, of the sirloin and of the middle of the ribs.

So designed this apparatus makes the measurements made upon the carcases comparable with one another and as far as possible objective, but it necessitates the intervention of an operator who places the carcase in position relative to the vertical frame and who displaces manually or by means of motors the several feelers.

The main aim of the invention is to provide an apparatus capable of carrying out automatically the measurement of the characteristics of the carcases from which their classification is effected, and then to determine automatically the classification of the carcases.

In what follows one is referring to the standardized European classification EUROPA. It is obvious that one skilled in the art will not have any difficulty in adapting the apparatus of the invention to another classification from the teaching provided by the invention.

SUMMARY OF THE INVENTION

An apparatus in accordance with the invention comprises a substantially vertical stand equipped with a frame having its position adjustable with respect to this stand, in the horizontal direction and in its slope with respect to the vertical, its bottom end being capable of being moved further away from the stand than its top end. In this frame a plate is mounted to be able to slide up and down in the said frame.

Within the spirit of the invention it is provided that the frame may be able to be aligned in a vertical plane and in a horizontal plane with respect to the stand in order to adapt its position to the contours of the half-carcases of different animals.

On its front face intended for being turned towards the half-carcase, the plate is provided with a stop projecting by about 5 to 6 cm, situated in the upper portion of it, preferably in the middle zone of it in the direction of the width and preferably offset with respect to the centre of the plate.

Comparators serving for the dorsal measurements (rump steak, sirloin, middle of the ribs) are mounted on one of the upright longitudinal edges of the frame; they can be displaced along this edge by respective individual driving means and at different speeds proportional to their maximum possible lengths of travel. Each of these comparators comprises, mounted upon a common support, a fixed feeler and a telescopic measuring feeler; this common support can be displaced in the transverse direction with respect to the plate.

Above the projecting stop the plate is equipped with a support carrying two feelers spaced apart in the vertical direction, one of which is fixed and the other telescopic for the said measurement of the topside; these feelers are situated in one and the same vertical plane which is spaced by a horizontal distance which is chosen between 50 and 100 mm from the plane passing through the centreline of the vertical stand, the frame and the plate. A vertical slit is arranged in the plate, substantially in the vertical plane of the feelers for measurement of the topside, at the level of the comparator for measurement of the middle of the ribs and on the extension of the travel of the latter in the vertical direction. A support projects through this slit in front of the plate, carrying two feelers directed horizontally in opposite directions and suitable for being extended in order to come to a stop, one against the sternum, the other against the spinal column of a carcase and thus measuring the width l. The support of these two feelers is joined to the comparator for measurement of the rib and can be displaced with it in the vertical direction.

As just defined the apparatus of the present invention enables the measurements to be carried out automatically.

These measurements are in accordance with the European classification which contains on the one hand a notion of contour depending upon the measurement of the profile, and on the other hand upon a state of fattening.

However, it is desirable to be able to have available an appreciation of the correlation between the contour and the percentage of the muscular masses.

In accordance with the present invention one can arrive at it by completing the measurement of the profile by a measurement of the thickness of the masses and by adding to the parameters a measurement of the size of the skeleton of the half-carcase.

The measurement of the thickness of the masses may be obtained by the measurement at a constant level, of the length of the processes, called in professional language the width of split.

For this purpose, in accordance with a supplementary improvement upon the present invention, the projecting stop is provided on the side of it intended for being turned towards the spinal column, with a rounded feeler the role of which is to come into contact with the heads of the vertebrae. The difference in position in the direction transverse to the half-carcase, between this rounded feeler and the feeler touching the end of the lumbar processes at the time of the measurement of the sirloin, is representative of the width of split.

The size of the skeleton of the half-carcase is represented significantly by the development of the heads of the vertebrae which may be appreciated on the one hand by the said measurement of length L provided by the distance between the feelers for measurement of the topside and the feelers for measurement of the width 1 already described above, and on the other hand by the measurement of the thickness of the vertebrae.

For carrying out this latter measurement, there exists in the plate a horizontal slit extending from the projecting stop, substantially at the level of the rounded feeler mounted on this plate, in the direction of the edge where there are the feelers for the dorsal measurements. In this slit there is mounted a movable finger the endface of which is flush with the face of the plate and which carries on this face a ball which is pushed back by a spring between a retracted position and a projecting position. The amount of movement of this finger is measured, for example, by means of a potentiometer to which the finger is connected. This movement can express directly or may serve to calculate with respect to the end of the rounded feeler the thickness of the vertebrae.

Without any restrictive intention and without excluding any variant, a description will now be given of an embodiment. Reference will be made to the attached drawings in which:

DESCRIPTION OF THE PREFERRED EMBODIMENT

Figure 2:
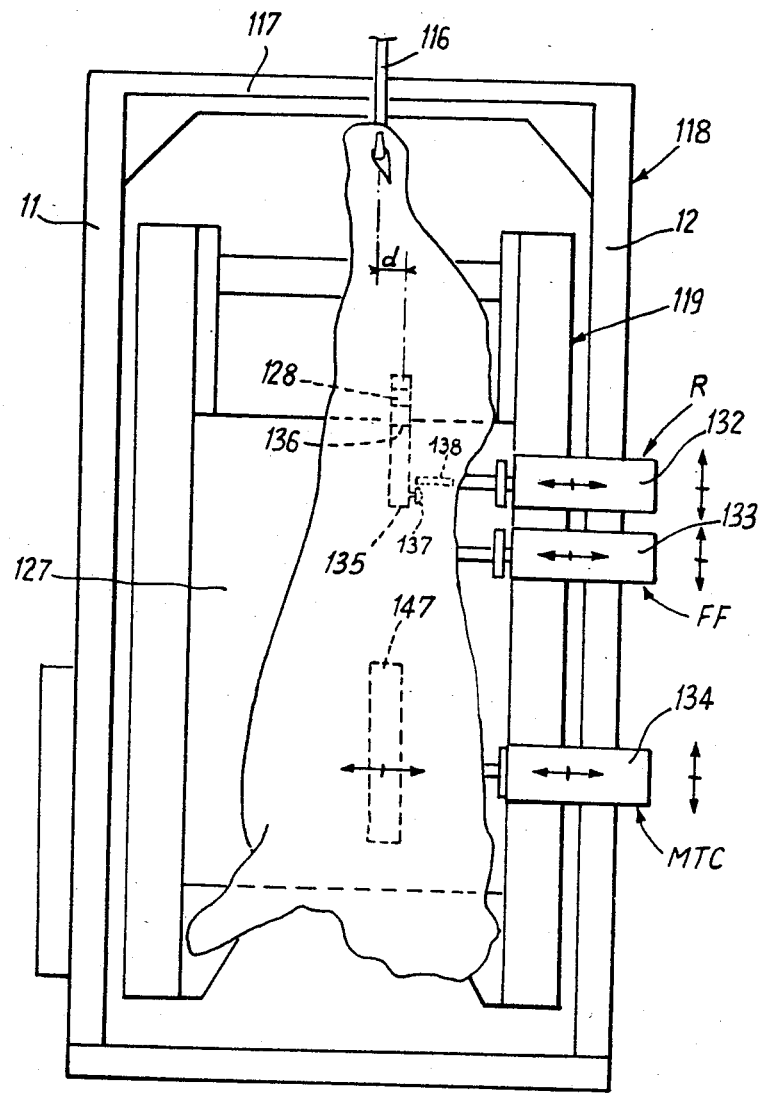
FIG. 2 is a front view of the same apparatus with a half-carcase of beef represented to show the position of it with respect to certain feelers and comparators.

Here the word half-carcase is employed for designating the body of the slaughtered animal which has been split in two exactly through the centre of its spinal column as is usual. Each half-carcase is hung by a hook 116 (FIG. 2) from a conveyor and it is stopped opposite the apparatus of the invention with the geometric axis of this hook 116 situated in the vertical plane lying at equal distances from the vertical uprights 11, 12 of the apparatus. The latter are joined at the top by an upper crossbar 117. A vertical supporting stand 118 is thus obtained, anchored solidly to the floor, upon which a frame 119 is mounted with a possibility of adjustment of its position in the horizontal direction and a slope towards the front of the vertical stand 118 in the direction of the half-carcases. This slope may be about 20°, the bottom portion of the frame 119 being further from the vertical stand 118 than the top portion of it.

In this example the frame 119 is carried by top and bottom bellcranks 120, 121 respectively which are hinged onto the vertical stand 118 about horizontal axes 122, 123 and which are connected by connecting-rods 124, 125 to a motor 126; thus the frame 119 is movable simultaneously in displacement in the horizontal direction and in its slope. It has dimensions less than those of the stand and it may be drawn back and retracted inside the latter.

In the frame 119 a plate 127 is mounted, the length of which is less than the latter and the position of which is adjustable by sliding in the direction vertical and longitudinal to this frame, thanks to a motor 128 fixed to the top of the said frame.

On one and the same vertical longitudinal edge of the frame 119 there are mounted comparators of dorsal measurements, being in succession from top to bottom; the comparator for measurement of the rump steak R, the comparator for measurement of the sirloin FF, and the comparator for measurement of the middle of the ribs MTC. Each of these comparators comprises a support 128, a feeler of fixed length 129, a telescopic measuring feeler 130 comprising, for example, a potentiometer or a measuring solenoid. Each support 128 can be displaced by sliding along the edge of the frame 119, individually under the action of a respective motor-gear-brake unit associated with an endless screw, for example. These units are grouped at 131 at the bottom of the frame 119. Each motor drives the corresponding support 128 from the bottom upwards at a speed which is proportional to its maximum possible length of travel. These lengths of travel are determined as a function of the species of the half-carcases and of the positions of the chosen points of measurement. When the supports 128 are stopped after a certain length of travel as will be explained later, they are displaced in the direction transverse to the plate 127 thanks to transverse means of guidance (not shown) housed in the thickness of the plate, under the action of respective individual motors 132, 133, 134 attached to the longitudinal edge of the frame 119.

Figure 3:
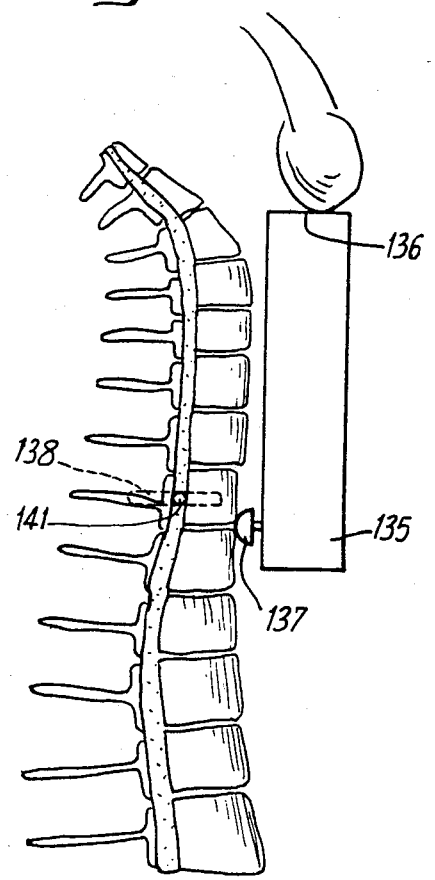
FIG. 3 is a detail on a larger scale, seen from the front of the apparatus in order to show how the measurement of the thickness of the vertebrae is carried out.
Figure 4:
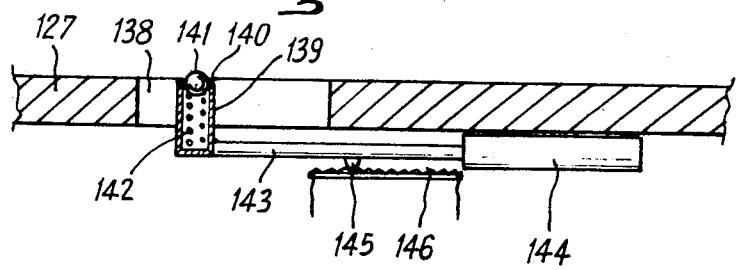
FIG. 4 is a detail on a larger scale in section along IV—IV from FIG. 1, showing the finger equipped with a ball and its means of manipulation.

To the upper portion of the plate 127 is attached a projecting stop 135 having an upper reference face 136. It projects by an amount of about 50 to 60 mm. It lies in the middle zone of the plate but offset by a distance d which is chosen to be between 50 and 100 mm, with respect to the vertical plane equidistant from the uprights 11, 12 towards the comparators for dorsal measurements. On the sideface of it turned towards the latter the projecting stop 135 is equipped with a rounded feeler 137. The latter is preferably a measurement feeler of telescopic type. On this same side of the projecting stop 135 a horizontal slit 138 starting from the latter extends towards the edge where there are the comparators for dorsal measurements, slightly above the level of the rounded feeler 137 (FIG. 3). A hollow finger 139 (FIG. 4) is arranged in this slit 138 with an endface 140 which is flush with the front face of the plate 127 and with respect to which a ball 141 which is pushed back by a spring 142 housed in the hollow finger 139 may have a projecting position and a retracted position. This finger 139 can be displaced along the slit 138; it is carried by a rod 143 of a jack 144 attached to the rear of the plate 127. The rod 143 carries a cursor 145 of a potentiometer 146. Any other equivalent means of measurement of the position of the finger 139 in the slit 138 might be employed. The arrival of the ball 141 in the medullary channel may be detected either by the resistance which it then opposes to the force of the jack 144 in the direction of its extension, or by a micro-contact housed in the finger 139 and controlled by the ball 141 as a function of its position.

At the bottom of the plate 127, substantially on the vertical through the projecting stop 135 and corresponding with the travel of the comparator MTC, the plate 127 exhibits a vertical slit 147 through which projects a support 148 which is joined to the support 128 of the comparator MTC in oder to move with it. This support 148 carries two horizontal feelers 149, 150 which are turned in opposite directions and which are each suitable for being extended in order to come to a stop respectively, the first against the spinal column and the other against the sternum inside a carcase.

Above the projecting stop 135 in the same vertical plane as it, the plate 127 is provided with a topside comparator TT which also comprises like the other comparators a support 128, a fixed feeler 129 and a telescopic measuring feeler 130. The support 128 can be displaced perpendicularly to the plane of the plate 127 thanks to a motor-gear-brake unit 151 attached to the top of the said plate.

In all of the comparators described above, R, FF, MTC, TT, when their support is displaced in the direction of a carcase, the feeler of fixed length is intended to encounter a bone whilst the telescopic feeler is intended to encounter the muscle at a predetermined distance from the bone. The extension of the telescopic feeler when it is stopped when the resistance opposed by the muscle is sufficient, is measured and transmitted in the form of a signal.

More generally, all of the movements of displacement of the supports, the comparators, and the feelers, are measured by known means (potentiometers, solenoids, etc . . . ) and the signals are collected by a calculator which carries out the operations terminating in the classification of the carcase.

The operation of the apparatus of the invention is as follows.

Before explaining it, it will be called to mind that in known manner microswitches are located at the ends of the travels of the displaceable members; their closure and opening serve to check and to control the desired sequence of the movements.

A half-carcase hung by a hook 116 from an overhead conveyor is moved in front of the apparatus. In the latter the frame 119 is in the vertical position retracted inside the vertical stand 118. All of the comparators are in their position of rest which in general is their lowest or furthest back position. The part projecting furthest from the plate 127 is the stop 135 but it is not projecting with respect to the apparatus because of the retraction of the frame 119 into the vertical stand 118. In its movement of displacement in parallel with the plate 127, the suspended half-carcase passes at about one centimeter in front of the apparatus. When the hook 116 arrives opposite the middle of the latter it encounters a stop (not shown) which can be retracted later on but which stops it and which actuates a switch for starting up the apparatus.

The frame 119 undergoes a first displacement which puts the surface of the plate 127 at about one centimeter from the half-carcase. At this moment the projecting stop 135 is engaged inside the half-carcase. The plate 127 then rises at the same time as the supports 128 of the comparators R, FF, MTC. As has been said above, the latter are displaced individually at speeds proportional to their maximum travel. During the rising of the stop 135 with the plate 127 the rounded feeler 137 slides over the vertebrae. This feeler might be omitted. The stop 135 would then rub directly against the vertebrae and the sliding would be effected less easily.

The displacement upwards ceases when the upper reference face 136 of the stop 135 encounters the bone of the ischiopubic protuberance, as may be seen in FIG. 3.

At this moment the comparators R, FF, MTC and the feelers for the chest width 149, 150 which are displaced with the comparator MTC are lying at their level for measurement, as also is the comparator TT which is carried by the plate 127. In addition, the slit 138 extends across the spinal column when the apparatus comprises this improvement.

Figure 1:
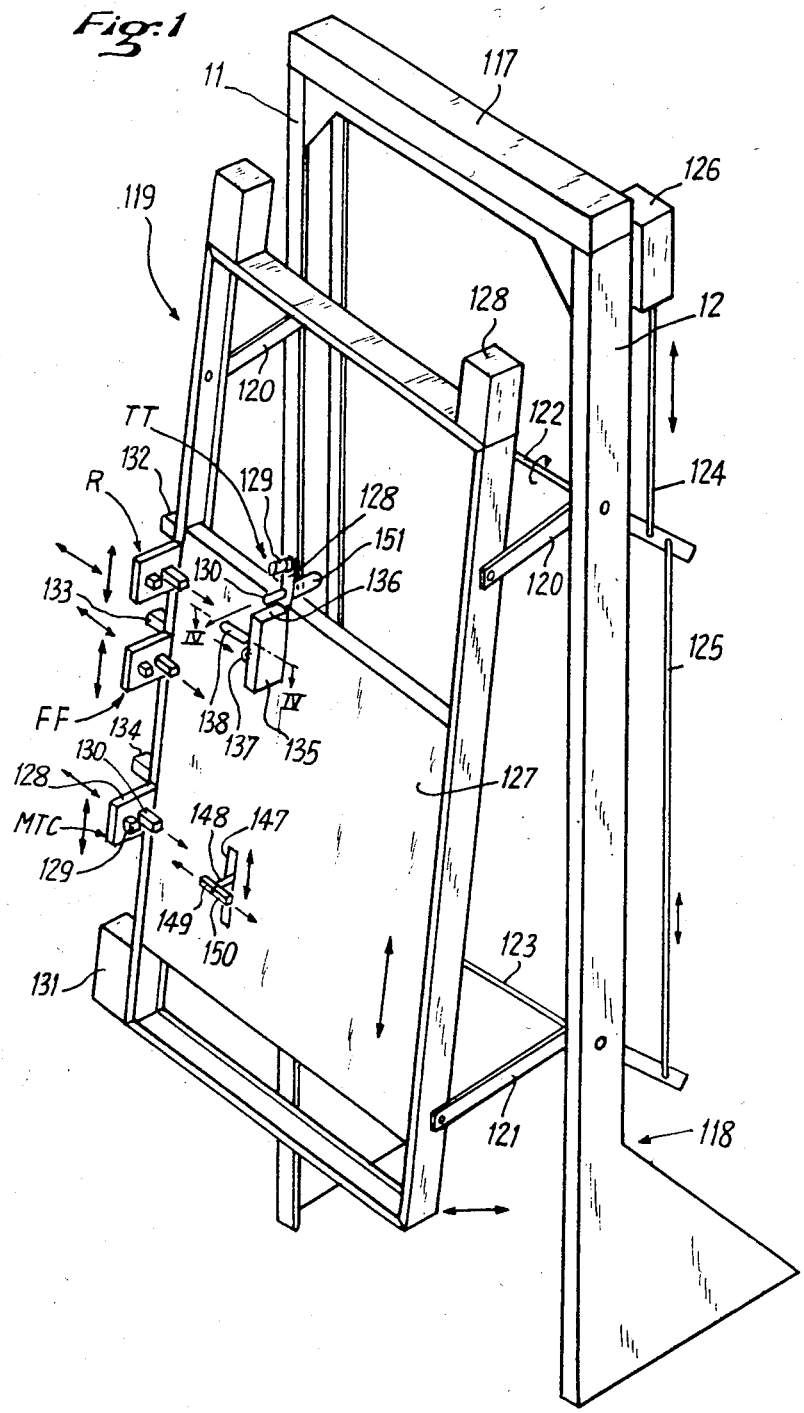
FIG. 1 is a general perspective of an apparatus in accordance with the invention seen from the front, that is to say, from the side at which a half-carcase should be found which is to be measured, represented in the position of use.

The frame 119 is then put in the position sloping towards the front by 20° with respect to the vertical as may be seen in FIG. 1. It pushes back the half-carcase which was hanging and which is resting completely against the plate 127 under the effect of the thrust. In this way the half-carcase adopts a definite position which is repeated for all of the half-carcases. The deformations which the latter may exhibit as a consequence of their own individual contour or of their suspension, are eliminated.

Under these conditions the comparators and the feelers may be set in action by way of the motors 132, 133, 134 and 151 so that the corresponding fixed feelers 129 come into contact with the bones at which they are aimed; when this contact is established, the telescopic measuring feeler is in contact with the muscle corresponding with this bone. It has undergone a contraction which is measured. The difference in position of the ends of the fixed 129 and telescopic 130 feelers of one and the same comparator enables reliable numerical data to be taken off, which can be employed for the automatic and objective classification of each half-carcase.

It will be observed that it is quite possible to reverse the relative position of the fixed feeler 129 and of the telescopic feeler 130 of each comparator by providing a fixed feeler 129 longer than the telescopic feeler 130, contrary to what is shown on the drawings. In this case each telescopic feeler comprises any suitable motor which is capable of extending it and retracting it. When the longer fixed feeler 129 has encountered the bone opposite which the comparator is lying, the latter ceases to be displaced and the motor of the telescopic feeler extends the latter as far as its encounter with the muscle.

The data taken off are expressed by signals emitted in relation to the displacements and the positions of the feelers. A calculator receives these signals and carries out the necessary calculations when the measurement taken does not express directly a classification characteristic. This calculator displays the result, that is to say, the classification of the half-carcase being considered, and possibly operates an automatic marking device.

With the basic embodiment of the apparatus of the invention, the following classification measurements are effected:

measurement of the rump steak directly by the comparator R which has been raised first of all to the level of the measurement;

measurement of the sirloin directly by the comparator FF which has been raised first of all to the level of the measurement;

measurement of the middle of the ribs directly by the comparator MTC which has been raised first of all to the level of the measurement;

measurement of the topside directly by the comparator TT which is lying in its position for measurement when the projecting stop 135 has been stopped by the ischiopubic protuberance;

measurement of the length L obtained by the difference between the vertical distance between the level at which the comparator MTC has been stopped and the reference surface 136 of the projecting stop 135 when the latter encounters the ischiopubic protuberance;

measurement of the chest width 1 obtained by the addition of the displacements of the feelers 149 and 150, the one as far as the spinal column, the other as far as the sternum, after their having been raised up to the level of measurement.

With the supplementary improvement in the apparatus it carries out in addition the following measurements:

width of slit (or of the spinal column) obtained by the difference between the position of the telescopic rounded feeler 137 which rubs against the vertebrae and the position of the feeler touching the ends of the lumbar processes when the comparator FF has been raised first of all to its level for measurement;

thickness of vertebra obtained by the position of the finger 139 when the ball 141 has entered the medullary channel, taking into account the position of the telescopic rounded feeler 137.

The description given above refers to half-carcases of beef. The apparatus of the invention is suitable also for the classification of half-carcases of other animals of comparable size (horses, for example) but it may in addition be adapted to the automatic classification of animals of small size (sheep, pigs, goats) the carcases of which are not split into half-carcases but remain whole. The concept of the apparatus remains the same. The only difference is that the projecting stop 135 is driven downwards with the plate 127 until it encounters the carcase between the animal's legs. The comparators R, FF and MTC are displaced downwards too. The exact position of the feelers is adapted accordingly, the important one being that the projecting stop 137 encounters by a predetermined reference face a predetermined point on the carcase.

We claim:

1. An apparatus for measurement of the classification characteristics of the carcases of animals slaughtered for meat, comprising a vertical supporting stand (118) equipped with means of positioning the half-carcases of these animals and with displaceable feeler means, characterized in that the vertical supporting stand (118) is equipped with a frame (119) the position of which is adjustable in the horizontal direction and in its slope with respect to the vertical, its bottom end being further from the vertical stand (118) than its top end, a plate (127) is mounted to slide up and down this frame (119), a projecting stop (135) having a reference face (136) is attached at the upper portion of the plate (127) to its front face which is intended for being turned towards the half-carcases which are to be measured, and this frame (119) carries the various displaceable means comprising measuring feelers which have members emitting signals in relation to their displacements and their positions, the projecting stop (137) being arranged on the plate (127) in order that its reference face shall encounter a predetermined point such as the bone of the ischiopubic protuberance when it is a question of a half-carcase, in consequence of the sliding of the plate (127) in the frame (119).

2. An apparatus as in claim 1, characterized in that for carrying out dorsal measurements upon the half-carcases, an upright longitudinal edge of the frame (119) is equipped with dorsal comparators for measurement of rump steak (R), sirloin (FF) and the middle of the ribs (MTC), spaced from the top of the plate downwards and displaceable along this edge at respective speeds as a function of their maximum lengths of travel, each comparator comprising a support (128) carrying at least one feeler (129) of fixed length and one telescopic measuring feeler (130), each support (128) being displaceable in the direction transverse to the plate (127) and the movements of the three supports (128) along the longitudinal edge of this frame being carried out simultaneously with the displacement of the plate (127) in the frame (119).

3. An apparatus as in claim 1, characterized in that for carrying out the measurement of the chest width a vertical slit (147) is arranged in the plate (127), this vertical slit (147) allowing a support (148) to pass through, which is displaceable along this slit and carries two telescopic measuring feelers (149, 150) arranged for being extended transversely to the plate (127) in opposite directions until touching the spinal column and the sternum respectively of the half-carcases placed upon the apparatus.

4. An apparatus as in claim 3, characterized in that the support (148) of the feelers (149, 150) for the chest width measurement is joined to a support (128) of comparator for measurement of the middle of the ribs (MTC) in order to be displaced at the same time as the latter.

5. An apparatus as in claim 1, characterized in that for carrying out the topside measurement (TT) a comparator is mounted on the plate (127) with a support (128) carrying at least one feeler of fixed length (129) and a telescopic measuring feeler (130), these two feelers (129, 130) extending perpendicularly to the plate (127) in the direction of the half-carcases which are to be measured and the support (128) being displaceable in this direction under the action of driving members (151).

6. An apparatus as in claim 5, characterized in that the projecting stop (135) and the comparator for measurement of the topside (TT) lie in one and the same vertical plane, the projecting stop (135) being below the comparator.

7. An apparatus as in claim 1, characterized in that a hook (116) for suspension of a half-carcase which is to be measured, having been stopped in a plane situated at equal distances from two uprights (11, 12) forming part of the vertical stand (118), the vertical plane containing the projecting stop (135) is spaced by a distance (d)

chosen to be between 50 and 100 mm, away from the plane containing the said hook (116).

8. An apparatus as in claim 1, characterized in that the projecting stop (135) is provided on one sideface of it with a rounded feeler (137) of telescopic measuring type intended for sliding against the vertebrae of a half-carcase which is to be measured.

9. An apparatus as in claim 8, characterized in that a horizontal slit (138) is arranged in the plate (127) in order to let a finger (139) pass through, which has an endface (140) flush with the front face of this plate (127) and contains a ball (141) which is pushed back by a spring (142) between a retracted position and a projecting position in which this ball (141) can enter the medullary channel, this finger (139) being displaceable along the horizontal slit (138) under the action of a jack (144) provided with a means (145, 146) of measurement of the displacement of the said finger (139).

10. An apparatus as in claim 1, characterized in that the frame (119) has dimensions less than those of the vertical stand (118) and it is suspended by levers (120, 121) hinged about pins (122, 123) carried by the vertical stand (118) and coupled by connecting-rods (124, 125) to a driving member (126), the frame (119) being displaceable as far as a withdrawn position in which it is retracted into the vertical stand (118).

* * * * *